United States Patent [19]

Kelman

[11] Patent Number: 4,828,558
[45] Date of Patent: May 9, 1989

[54] LAMINATE OPTIC WITH INTERIOR FRESNEL LENS

[76] Inventor: Charles D. Kelman, 269 Grand Central Pkwy., Floral Park, N.Y. 11005

[21] Appl. No.: 78,558

[22] Filed: Jul. 28, 1987

[51] Int. Cl.$^4$ ............................................. A61F 2/16
[52] U.S. Cl. ....................................... 623/6; 351/166; 351/171; 351/172
[58] Field of Search .............. 623/6; 351/166, 168–172

[56] References Cited

U.S. PATENT DOCUMENTS

| 4,074,368 | 2/1978 | Levy, Jr. et al. | 623/6 |
| 4,534,069 | 8/1985 | Kelman | 623/6 |
| 4,673,406 | 6/1987 | Schlegel | 623/6 |

FOREIGN PATENT DOCUMENTS 0212616  3/1987  European Pat. Off. ................ 623/6

Primary Examiner—Ronald L. Frinks
Attorney, Agent, or Firm—Henry Sternberg; Bert J. Lewen

[57] ABSTRACT

Composite lens, especially an intraocular lens for insertion through an incision into an eye and desirably containing haptics, comprising a flat, partially hollow laminate optic, formed by a pair of relatively thin, sheet-like elements having opposed interior surfaces, at least one such element constituting a protected Fresnel lens defining the interior surface of the element as a discontinuous surface formation of a concentric series of annular prisms, the interior surfaces being peripherally sealed together to define therebetween a counterpart series of permanent captive gas enclosing, liquid free, spaces of different index of refraction from that of the elements, preferably with the elements being formed of flexible, temporarily deformable material and together sized to provide the optic with a comparatively thin thickness in relation to its diameter, permitting its deformation into a reduced girth cylindrical shape for eye insertion through a minimum size corneal incision, after which the lens will return to its original state for seating in place in the eye.

15 Claims, 1 Drawing Sheet

U.S. Patent  May 9, 1989  4,828,558
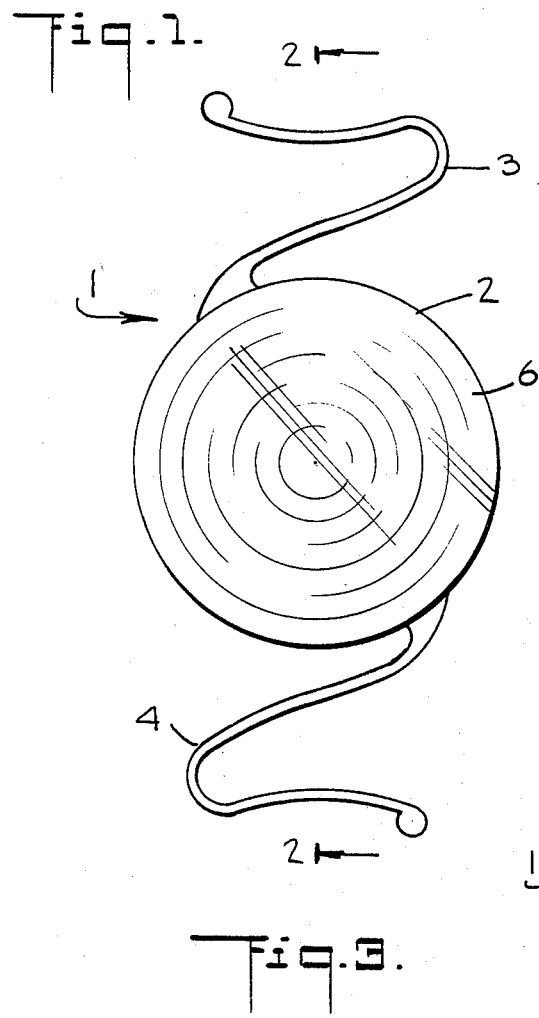
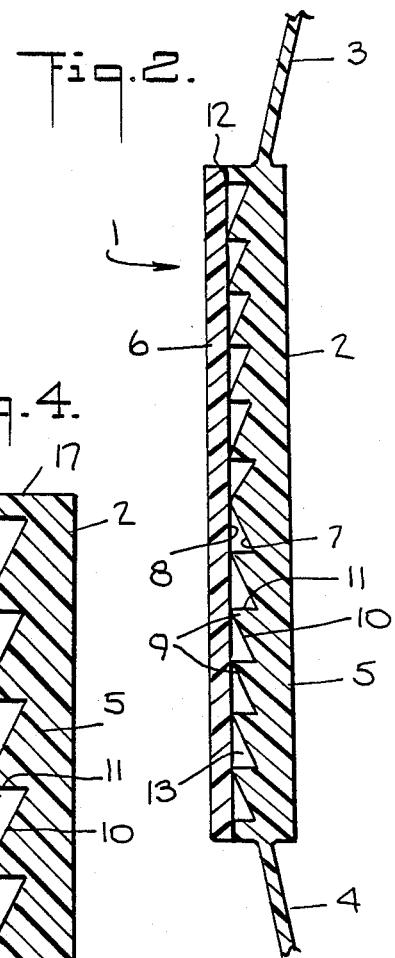
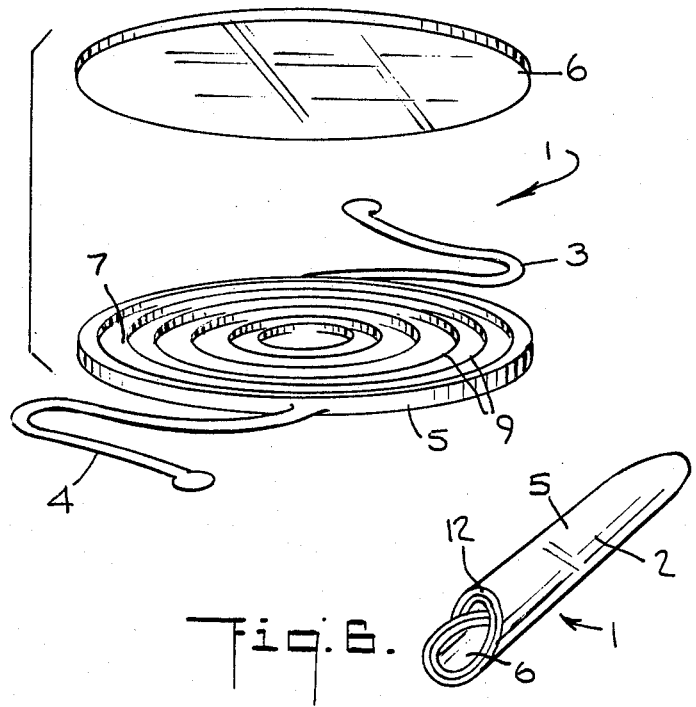
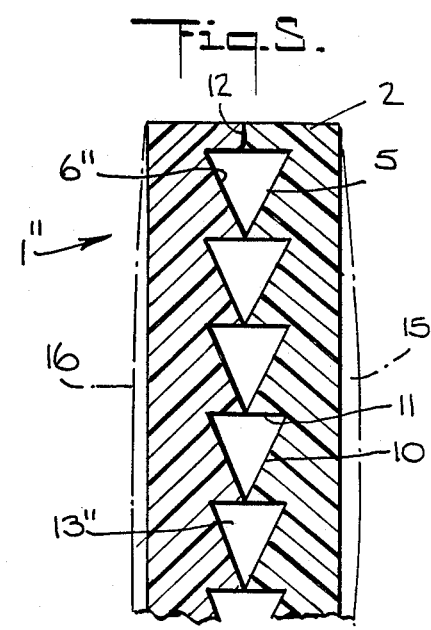

LAMINATE OPTIC WITH INTERIOR FRESNEL LENS

FIELD AND BACKGROUND OF THE INVENTION

The present invention relates to a laminate optic with an interior Fresnel lens, and more particularly to an artificial composite intraocular lens for insertion into an eye through a corneal incision of minimal size, having a partially hollow laminate optic of flexible, temporarily deformable material, including a pair of opposed interior surfaces, at least one of which is formed as a protected internal Fresnel lens, and both of which together define captive gas spaces therebetween.

For treatment of conditions such as natural eye lens cataracts, a known eye surgery procedure is to remove the cataracted lens through an incision in the wall of the cornea of the eyeball, and replace it by an artificial intraocular lens as an internal implant lens. Intraocular lenses are often made of flexible material such as silicone plastic to permit reduction of their overall apparent girth by temporary deformation for facilitating their insertion through the cornea, thereby advantageously enabling use of a corneal incision of concomitantly reduced size.

Such intraocular lenses often have haptics extending from the periphery of their optics, i.e. normally expanded resilient appendages connected to the central lens body or optic, to aid lens seating in the eye. Preferably, these haptics should also be kept in contracted state during insertion of the lens into the eye to enable the lens unit to fit without difficulty through a minimum size incision.

U.S. Pat. No. 4,573,998 to Mazzocco and U.S. Pat. No. 4,534,069 to Kelman are among typical proposals offered to provide the flexible optic and/or haptics of such an intraocular lens in temporarily reduced girth condition for incision insertion purposes.

However, known optics of flexible material, such as silicone rubber or plastic, have the distinct drawback that in order to achieve the desired optical characteristics of the particular intraocular lens, the optic must be made relatively thick, as measured along the optical axis, thereby increasing its mass and volume.

Consequently, the sought advantage of forming the optic of flexible material, e.g. providing a silicone optic, which would otherwise permit the optic to be deformed by curling, folding or the like, into a generally cylindrical shape of sufficiently small apparent girth to fit through a minimum length corneal incision, cannot be achieved. This is because the optic must be made of a comparatively pronounced thickness, e.g. 3 mm, for purely optical reasons, and therefore is of such mass and volume that it cannot readily be curled, folded, etc. into a small enough generally cylindrical shape to accomplish the underlying purpose of forming the optic of flexible material, i.e. to exploit the use of a minimum size incision.

A Fresnel lens is a known type of lens which is greatly reduced in weight by dividing the continuous lens surface into a succession of concentric rings, assembled in correct relationship on a generally flat surface. More specifically, it is a compound lens of annular prisms, providing a stepped lens of less weight and thickness than, for example, a corresponding plano-convex lens, with the risers of the steps desirably set at such an angle as to present no disturbance to the light rays. An advantage of such a Fresnel lens is that its collection angle is generally much greater than practicable for a solid type, e.g. plano-spheric, lens.

U.S. Pat. No. 4,673,406 to Schlegel is a recent proposal concerning the inclusion of an exterior Fresnel lens formation on the deformable lens body or optic of an artificial intraocular lens, made of a homogeneous, crystal-clear, high-temperature resistant plastic, preferably vulcanized silicone, to enhance the optical characteristics of the system while reducing the optic thickness. Specifically, the exterior Fresnel lens formation is configured with a circular central portion and at least one annular portion immediately surrounding and backwardly offset from the central portion to reduce the thickness of the lens body and facilitate its folding during lens implantation into the eye. However, once inserted in the eye, the surrounding aqueous humor in the eye interior coats the exterior Fresnel lens formation and detracts from the optical effectiveness thereof, since the aqueous humor has an index of refraction sufficiently close to the index of refraction of the intraocular lens material that the optical characteristics of the Fresnel lens are detrimentally offset.

It would be desirable to provide a deformable intraocular lens for insertion into the eye to achieve the above noted overall advantages, especially the use of a minimum size corneal incision, yet which has a Fresnel lens formation which is protected from the adverse effects on its optical characteristics of the aqueous humor environment inside the eye.

SUMMARY OF THE INVENTION

It is among the objects and advantages of the present invention to overcome the drawbacks and deficiencies of the prior art, and to provide a composite lens in the form of a partially hollow laminate optic, protectively containing an interior Fresnel lens and attendant interior surface defined captive gas enclosing, liquid free, spaces thereat of different index of refraction from that of the optic.

It is among the additional objects and advantages of the present invention to provide a composite lens of the foregoing type, in the form of an artificial intraocular lens of flexible, temporarily deformable, material, sized to provide the optic with a comparatively thin thickness to permit its deformation into a generally cylindrical shape of reduced apparent girth capable of insertion into an eye through a minimum size corneal incision, yet which will readily return to its original, expanded and undeformed state, while retaining its desired optical characteristics, once it is inside the eye, enabling the lens to be seated properly therein by the surgeon.

It is among the further objects and advantages of the present invention to provide a composite lens of the stated type which can be made from readily available materials, which is relatively safe and durable in use, and whose Fresnel lens optical characteristics are not adversely affected by the aqueous humor environment inside the eye.

According to the present invention, a composite lens is provided, which comprises a generally flat, partially hollow, unitary laminate optic, formed by a pair of opposed, relatively thin, sheet-like elements of conforming perimetric shape and of selective index of refraction, and having a corresponding pair of opposed interior surfaces. At least one of the elements comprises a protected internal Fresnel lens defining the interior surface of the element as a discontinuous surface formation including a concentric series of annular prisms composed of optical step areas interconnected by offset riser areas. The interior surfaces are peripherally sealed together to define therebetween a counterpart concentric series of permanent captive gas enclosing, liquid free, annular spaces of different index of refraction from the selective index of refraction of the elements.

More particularly, the present invention contemplates a composite intraocular lens for insertion through an incision in an eye, which comprises such a generally flat, partially hollow, unitary laminate optic, formed by a pair of opposed, relatively thin, sheet-like elements of the stated type. The elements are specifically of flexible, temporarily deformable material, and together are sized to provide the optic with a comparatively thin thickness in relation to its diameter sufficiently to permit temporary deformation of the optic into a generally cylindrical shape of reduced apparent girth capable of insertion into the eye through a minimum size incision.

Preferably, the elements are wafer thin, and air is enclosed in the annular spaces as captive gas. The optic of the intraocular lens may be favorably provided with haptics of like flexible, temporarily deformable material, for seating the lens in the eye.

BRIEF DESCRIPTION OF THE DRAWINGS

Other and further objects and advantages of the present invention will become apparent from the within specification and accompanying drawings, in which:

FIG. 1 is a plan view of a composite intraocular lens having a laminate optic of flexible material, formed by a pair of opposed relatively thin sheet-like elements, and provided with haptics, in accordance with one embodiment of the present invention;

FIG. 2 is an exaggerated sectional view taken along the line 2—2 of FIG. 1;

FIG. 3 is a perspective exploded view of the lens of FIG. 1, showing one of the elements as a wafer thin Fresnel lens and the other of the elements as a wafer thin cover for the Fresnel lens;

FIGS. 4 and 5 are enlarged, exaggerated partial sectional views of two corresponding modified laminate optic embodiments of the composite lens of the present invention; and FIG. 6 is a schematic perspective view showing the manner of deforming the composite lens of the present invention into a generally cylindrical shape of reduced apparent girth capable of insertion through a minimum size corneal incision into the interior of the eye.

DESCRIPTION OF THE PREFERRED EMBODIMENTS

Referring to the drawings, and initially to FIGS. 1-3, a flexible, temporarily deformable, artificial intraocular lens 1, according to one embodiment of the present invention, is shown, which is curlable, foldable, or otherwise deformable, into a reduced girth form for insertion into the interior of an eye through a corneal incision of minimized size, as an implant for replacing the natural lens, such as a cataracted lens.

Lens 1 comprises a generally flat, partially hollow, unitary light focusing lens body or laminate optic 2, and is desirably provided with a symmetrical pair of position fixation means or haptics 3, 4 or the like, i.e. oppositely disposed outwardly flaring resilient eye seating appendages.

Haptics 3, 4 or the like may be integrally connected to optic 2, and are used for embracing the adjacent portions of the eye interior for seating lens 1 in the usual manner, e.g. in the anterior chamber, in the posterior chamber, or in the posterior capsule, as the case may be, depending on the contemplated surgical procedure, once the intraocular lens has been inserted through the incision in the cornea and positioned for such seating.

Laminate optic 2 is formed by the pair of opposed, relatively thin, sheet-like elements 5 and 6 of conforming perimetric, e.g. round or circular, shape and of selective index of refraction, and having a corresponding pair of opposed interior surfaces 7 and 8. In the embodiment shown in FIGS. 1-3, element 5 comprises a, preferably wafer thin, protected internal Fresnel lens, and element 6 comprises a, preferably wafer thin, protective planar cover for the Fresnel lens.

Elements 5 and 6 are preferably formed of plastic material, and haptics 3, 4 are likewise preferably formed of plastic material.

As may be appreciated from FIGS. 2-3, the Fresnel lens element 5 defines the interior surface 7 thereof as a discontinuous surface formation, which includes a concentric series of annular prisms 9 composed of annular refraction, i.e. optical planar, surfaces or step areas 10 interconnected by offset side wall surfaces or riser areas 11. In turn, the complemental cover element 6 has a generally flat, smooth interior surface 8 arranged for overlying disposition on the Fresnel lens interior surface 7.

Interior surfaces 7 and 8 are suitable peripherally sealed together, e.g. by heat sealing, to form a bond or seal 12, so as to define therebetween a counterpart concentric series of permanent captive gas enclosing, liquid free, annular spaces 13 of different index of refraction from the selective index of refraction of elements 5 and 6. At the same time, seal 12 interconnects elements 5 and 6 to provide a peripherally integral laminate optic 2. As will be appreciated, any appropriate means may be used to achieve the peripheral sealing of elements 5 and 6 together at their opposed interior surfaces 7 and 8 for forming the integral laminate optic 2.

The captive gas enclosed in annular spaces 13 may be air or other appropriate gas, so long as the resulting index of refraction in spaces 13 is different from that of elements 5 and 6. In this regard, it will be appreciated that although the index of refraction of elements 5 and 6 may differ from one another, it is often preferred that the two elements have substantially the same index of refraction, depending on the optical characteristics sought for laminate optic 2, yet in either case the composite lens 1 must still have an index of refraction in the liquid free spaces 13 which is distinctly different from that of each of elements 5 and 6.

FIG. 4 shows a first modification embodiment in which the composite lens 1' is provided with a similarly preferably wafer thin cover element 6', but in this instance having a slight optical curvature containing exterior 14 on cover element 6' to enhance the desired optical properties of the optic.

FIG. 5 shows a second modification embodiment in which the composite lens 1'' is provided with a cover element 6'' in the form of a coacting Fresnel lens element to element 5, e.g. as a complementary or duplicate such element. In this case, the concentrically ridged or annular prism discontinuous surfaces of both Fresnel lens elements are in contact with one another and contribute to provide even larger corresponding counterpart captive gas enclosing annular spaces 13".

Also shown in phantom in FIG. 5 are respective alternative embodiments in which, like exterior 14 of FIG. 4, one or both of the Fresnel lens elements 5 and 6" may be optionally provided with a slight optical curvature containing exterior 15 and/or 16, as the case may be, for analogous enhancement of the optical properties of the particular resultant optic.

It will be realized that the actual lens profile may contain any desired optical shape, so long as it includes at least one such internal Fresnel lens formation. Thus, any optical curvature may be formed on the exterior of one or both of elements 5 and 6 so as to provide the composite lens, for example, as a double convex, plano-convex, convex meniscus, double concave, plano-concave, or concave meniscus, profile type lens, depending on the desired optical properties, while still enjoying the basis advantages of the included internal Fresnel lens formation.

As shown in FIG. 5, in order to assure permanent, e.g. hermetic, sealing of the peripheries of elements 5 and 6", an appropriate peripheral end wall extension 17 may be provided on one (or both) of the elements for proper interconnection at the interior surface locations of bond or seal 12.

FIG. 6 shows the manner of curling or otherwise deforming composite intraocular lens 1 (or lens 1' or 1"), e.g. in the manner of a sheet of paper, into a generally cylindrical shape of reduced apparent girth capable of insertion into the eye through a minimum size incision, in accordance with surgical procedures well known to those skilled in the art. It will be seen from the various embodiments of FIGS. 1-5 that the two elements are together sized to provide optic 2 with a comparatively thin composite thickness, i.e. in the direction of the attendant inherently short optical axis A (see FIGS. 1-2), in relation to the diameter thereof, which is sufficient to permit temporary deformation of optic 2, as well as of any attendant haptics 3, 4, for the desired girth reduction purposes.

In this regard, in accordance with one preferred feature of the present invention, optic 2 may be provided with a thickness of at most about 1.5-2 mm, and a diameter of at most about 6 mm, whereupon the reduced girth, generally cylindrical shape, deformed composite lens, including any attendant haptics, will be able to be inserted into the eye readily and relatively safely through a corneal incision of only about 3 mm length, after which the composite lens can be allowed to expand to its original size and undeformed state, while retaining its desired optical characteristics, for appropriate seating in the eye in normal manner by the surgeon.

As to haptics 3, 4, these may have a thickness of about 0.2 mm and a width, i.e. in the plane of the paper of FIG. 1, of about 1.2 mm. Haptics 3, 4 may be of any suitable shape well known in the art and may have a maximum composite expanded length dimension in normal, non-contracted condition of about 13 mm from the outer edge or crest portion of one haptic to the diametrically opposite outer edge or crest portion of the other haptic in the elongate direction as shown in FIG. 1.

A distinct feature and advantage of the present invention is that the integral composite laminate optic 2 contains a permanently sealed, and thus leakproof, captive gas chamber or separation space, which internally protects the at least one Fresnel lens present in the lens interior from any contact with, and in turn from the otherwise adverse effects on the Fresnel lens basic optical characteristics of, the surrounding aqueous humor environment in the eye interior.

Another distinct feature and advantage of the present invention is that the presence of such captive gas chamber or separation space provides the lens with a more pliable physical construction of comparatively reduced mass and volume, enabling the relatively thin, integral laminate optic to be deformed more efficiently into the desired generally cylindrical shape and to a greater degree of apparent girth reduction.

A further distinct feature and advantage of the present invention is that, by reason of the presence of such captive gas chamber or separation space, the lens possesses a lower composite density than otherwise for its actual externally defined volume, which contributes a buoyant effect to its mass in the surrounding aqueous humor, that inherently beneficially reduces the weight or load exerted by the lens on the portions of the eye interior at which the lens is implanted.

Thus, the lens construction of the present invention permits the optical characteristics of a Fresnel lens, i.e. a relatively short focal length and short optical axis and a relatively large diameter, in a reduced thickness composite optic, to be exploited successfully by use thereof as an implant within the interior of an eye, without the previously encountered drawback of interference from surrounding eye fluids filling the spaces or grooves of the Fresnel lens discontinuous annular prism surface and detracting from the optical effectiveness thereof, due to the fact that the index of refraction of such fluids in direct contact with the Fresnel lens surface is not sufficiently different from the index of refraction of the material of the optic itself.

Lens 1 may be formed of any suitable light focusing optic serving material, which is sufficiently flexible for effecting the desired girth reduction, and whose desired at least two haptics or like appendages are likewise formed of flexible material for the same purpose as well as for permitting such appendages to perform in the contemplated lens positioning manner. Of course, any such flexible material used for the lens and for its desired appendages must be compatible with the environment in the interior of the eyeball, such as a non-toxic plastic, for example silicone or polymethylmethacrylate.

More particularly, for the purposes of the present invention, the material of lens 1 must be sufficiently flexible to permit its mass to be grossly deformed, e.g. with appropriate curling, folding, crinkling and the like of such mass, spatially inwardly in a direction to reduce its apparent composite girth, and preferably also to be deformed spatially longitudinally in the direction of its spatial dimension taken as its length.

The contemplated lens material is normally sufficiently flexible to have a temporary resilient memory, such that even if the lens mass is deformed to provide the same in compressed condition for reducing its girth, and maintained in such compressed condition for an extended period of time, it will thereafter still return readily to its original, expanded and undeformed state. Nevertheless, the period of time such mass is kept deformed under such compressed conditions should not be more than several hours to insure that there will be no permanent loss of such resilient memory.

Thus, according to the present invention, the artificial intraocular lens is preliminarily compacted into generally cylindrical form, which represents a conveniently shaped, small size girth, temporary insert element, which contains the lens and haptics, and which is capable upon insertion into the eye of returning to its original expanded size.

In this regard, the term "cylindrical" is used herein to comprehend not only a true right cylindrical geometric shape but also analogous elongate shapes, including those of out-of-round, oblate, and polygonal cross sectional profile, produced in any appropriate manner, as these shapes are likewise appropriate for enabling the reduced apparent girth composite lens to be inserted readily through the intended minimum size corneal incision safely and with minimum trauma or discomfort to the patient.

As to the actual insertion of the composite lens into the eye, since its cylindrical shape is of reduced girth form, the incision can be of greatly reduced size, and this insures that the procedure will be able to be carried out as safely as possible and with minimum trauma to the patient.

It should be noted that, while the composite lens of the present invention may be composed of any flexible, temporarily deformable, non-toxic and eye fluid compatible material, such as a plastic material, including in particular silicone, polymethylmethacrylate, and the like, with any associated haptic or the like position fixation members being of the same type material, or even a comparatively more flexible material such as polypropylene, nevertheless the very fact that the laminate optic is composed of relatively thin sheet-like, preferably wafer thin, elements, permits use of materials which are not normally considered particularly flexible or pliable.

More specifically, because of the contemplated very thin individual thicknesses of the sheet-like elements and their separation from each other by the intervening captive gas enclosing spaces bounded by the perimetric seal, otherwise less flexible plastic materials such as certain forms of polymethylmethacrylate, may still be used advantageously as the flexible material according to the present invention, due to their inherent ability as individual sheets to flex or bend out of their normal plane in the manner of curling, folding or otherwise deforming a sheet of paper, as compared to internal deformation within their own plane in the manner of physically compressing a pliable sponge.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Composite intraocular lens for insertion through an incision in an eye, which comprises a generally flat, partially hollow, unitary laminate optic, formed by a pair of opposed, relatively thin, sheet-like elements of conforming perimetric shape and of selective index of refraction, and having a corresponding pair of opposed interior surfaces, at least one of the elements comprising a protected Fresnel lens defining the interior surface of the element as a discontinuous surface formation including a concentric series of annular prisms composed of optical step areas interconnected by offset riser areas, and the interior surfaces being peripherally sealed together to define therebetween a counterpart concentric series of permanent captive gas enclosing, liquid free, annular spaces of different index of refraction from the selective index of refraction of the elements, and which collectively form a permanently sealed, leakproof, captive gas chamber which internally protects said Fresnel lens from any contact with the surrounding aqueous humor environment in the eye interior.

2. Lens of claim 1 wherein one of the elements comprises a wafer thin Fresnel lens and the other of the elements comprises a wafer thin cover for the Fresnel lens.

3. Lens of claim 1 wherein the two elements comprise coacting wafer thin Fresnel lenses.

4. Lens of claim 1 wherein a slight optical curvature is formed on the exterior of at least one of the elements.

5. Lens of claim 1 wherein the two elements have substantially the same index of refraction.

6. Lens of claim 1 wherein air is enclosed in the annular spaces as captive gas.

7. Lens of claim 1 wherein the elements are formed of flexible, temporarily deformable material.

8. Composite intraocular lens for insertion through an incision in an eye, which comprises a generally flat, partially hollow, unitary laminate optic, formed by a pair of opposed, relatively thin, sheet-like elements of flexible, temporarily deformable material, of conforming perimetric shape and of selective index of refraction, and having a corresponding pair of opposed interior surfaces, at least one of the elements comprising a protected Fresnel lens defining the interior surface of the element as a discontinuous surface formation including a concentric series of annular prisms composed of optical step areas interconnected by offset riser areas, the interior surfaces being peripherally sealed together to define therebetween a counterpart concentric series of permanent captive gas enclosing, liquid free, annular spaces of different index of refraction from the selective index of refraction of the elements, and which collectively form a permanently sealed, leakproof, captive gas chamber which internally protects said Fresnel lens from any contact with the surrounding aqueous humor environment in the eye interior, and the elements together being sized to provide the optic with a comparatively thin thickness in relation to its diameter sufficiently to permit temporary deformation of the optic into a generally cylindrical shape of reduced apparent girth capable of insertion into the eye through a minimum size incision.

9. Lens of claim 8 wherein one of the elements comprises a wafer thin Fresnel lens and the other of the elements comprises a wafer thin cover for the Fresnel lens.

10. Lens of claim 8 wherein the two elements comprise coacting wafer thin Fresnel lenses.

11. Lens of claim 8 wherein a slight optical curvature is formed on the exterior of at least one of the elements.

12. Lens of claim 8 wherein the two elements have substantially the same index of refraction.

13. Lens of claim 8 wherein air is enclosed in the annular spaces as captive gas.

14. Lens of claim 8 wherein the optic has a thickness of at most about 1.5–2 mm and a diameter of at most about 6 mm.

15. Lens of claim 8 wherein the optic is provided with haptics of flexible, temporarily deformable material.

* * * * *